(12) United States Patent
Beaver

(10) Patent No.: US 11,934,784 B2
(45) Date of Patent: *Mar. 19, 2024

(54) AUTOMATED SYSTEM AND METHOD TO PRIORITIZE LANGUAGE MODEL AND ONTOLOGY EXPANSION AND PRUNING

(71) Applicant: Verint Americas Inc., Alpharetta, GA (US)

(72) Inventor: Ian Roy Beaver, Spokane, WA (US)

(73) Assignee: Verint Americas Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/838,461

(22) Filed: Jun. 13, 2022

(65) Prior Publication Data
US 2022/0305085 A1 Sep. 29, 2022

Related U.S. Application Data

(63) Continuation of application No. 16/659,913, filed on Oct. 22, 2019, now Pat. No. 11,361,161.

(60) Provisional application No. 62/748,639, filed on Oct. 22, 2018.

(51) Int. Cl.
G06F 40/289 (2020.01)
A61K 31/198 (2006.01)
A61K 31/215 (2006.01)
A61K 31/216 (2006.01)
A61K 31/401 (2006.01)
A61K 31/41 (2006.01)
A61K 38/18 (2006.01)
G06N 20/00 (2019.01)

(52) U.S. Cl.
CPC ......... *G06F 40/289* (2020.01); *A61K 31/198* (2013.01); *A61K 31/215* (2013.01); *A61K 31/216* (2013.01); *A61K 31/401* (2013.01); *A61K 31/41* (2013.01); *A61K 38/1841* (2013.01); *G06N 20/00* (2019.01)

(58) Field of Classification Search
None
See application file for complete search history.

(56) References Cited

U.S. PATENT DOCUMENTS

| 6,385,579 | B1 | 5/2002 | Padmanabhan et al. |
| 2008/0046244 | A1 | 2/2008 | Ohno et al. |
| 2012/0131031 | A1 | 5/2012 | Xie et al. |
| 2015/0127652 | A1 | 5/2015 | Romano |

(Continued)

OTHER PUBLICATIONS

Galescu et al, "Bi-directional conversion between graphemes and phonemes using a joint n-gram model", 2001, In4th ISCA Tutorial and Research Workshop (ITRW) on Speech Synthesis 2001, pp. 1-6.

(Continued)

*Primary Examiner* — Quynh H Nguyen
(74) *Attorney, Agent, or Firm* — Meunier Carlin & Curfman LLC

(57) ABSTRACT

A system and method for updating computerized language models is provided that automatically adds or deletes terms from the language model to capture trending events or products, while maximizing computer efficiencies by deleting terms that are no longer trending and use of knowledge bases, machine learning model training and evaluation corpora, analysis tools and databases.

9 Claims, 2 Drawing Sheets

(56) References Cited

U.S. PATENT DOCUMENTS

| | | | |
|---|---|---|---|
| 2016/0078016 A1* | 3/2016 | Ng Tari | G16H 70/00 |
| | | | 707/723 |
| 2016/0078860 A1* | 3/2016 | Paulik | G10L 15/063 |
| | | | 704/244 |
| 2016/0117386 A1 | 4/2016 | Ajmera et al. | |
| 2016/0217127 A1 | 7/2016 | Segal et al. | |
| 2016/0217128 A1* | 7/2016 | Baum | G06F 40/289 |

OTHER PUBLICATIONS

Saon et al, "Data-driven approach to designing compound words for continuous speech recognition.", 2001, EEE transactions on Speech and audio processing. May 2001;9(4):327-32.

Summons to Attend Oral Proceedings received in European Application No. 19 204 698.5 dated Mar. 22, 2023, 9 pages.

Notice of Allowance received in U.S. Appl. No. 17/225,589, dated Jan. 12, 2023, 10 pages.

Final Office Action received in U.S. Appl. No. 17/838,459, dated Aug. 8, 2023, 19 pages.

\* cited by examiner

AUTOMATED SYSTEM AND METHOD TO PRIORITIZE LANGUAGE MODEL AND ONTOLOGY EXPANSION AND PRUNING

CROSS REFERENCE TO RELATED APPLICATIONS

This application is a continuation of U.S. patent application Ser. No. 16/659,913, pending, which is a non-provisional patent application claiming priority to Provisional Patent Application Ser. No. 62/748,639, filed Oct. 22, 2018, which are both hereby incorporated by this reference in their entireties as if fully set forth herein.

BACKGROUND

Field

Embodiments of the present invention relate to language models and ontologies, and more particularly, to a system and method for automatically prioritize language mode and ontology expansion and pruning.

Background

In speech recognition, a language model (LM) is a graph of probabilities associated to word transitions from a known vocabulary, such as a word lattice. Word embedding is the collective name for a set of language modeling and feature learning techniques in natural language processing (NLP) where words or phrases from the vocabulary are mapped to vectors of real numbers. Some approaches to language model development include term frequency inverse document frequency (TF-IDF) and word similarity. For instance, vocabulary in the insurance domain is expected to differ greatly from vocabulary in the telecommunications domain. To create a LM for use in a specific domain, texts are gathered from various sources such as websites, chat logs, call logs, documentation, and other sources in that domain, but each such domain may use different terms or syntax for the same meaning. There is a need for a system and method to automatically prioritize language model and ontology expansion and pruning.

BRIEF SUMMARY OF THE DISCLOSURE

Accordingly, the present invention is directed to a system and method for a system and method for automatically prioritize language mode and ontology expansion and pruning that obviates one or more of the problems due to limitations and disadvantages of the related art.

In accordance with the purpose(s) of this invention, as embodied and broadly described herein, this disclosure, in one aspect, relates to a computer product comprising computer executable code embodied in a non-transitory computer readable medium that, when executing on one or more computing devices performs a method of normalizing terminology and phrases within a language model for a language domain. The method includes receiving text from a plurality of platforms; determining whether the text includes a term in a stored data model; identifying if a term that does exist in the data model appears in a new context; passing the term in the new context to a human for determination if the term should be added to a training example in the new context for retraining the data model; if the term does not appear in the new context, checking the term for frequency of use in a known context and adding the term in the known context to the training example with a new priority if the frequency has reached a predetermined threshold; and recompiling the language model based on the term in context.

In another aspect, the disclosure relates to a method of adding terms to a language model based on use. The method includes receiving text from a plurality of platforms; determining whether the text includes a term in a stored data model; identifying if a term that does exist in the data model appears in a new context; passing the term in the new context to a human for determination if the term should be added to a training example in the new context for retraining the data model; if the term does not appear in the new context, checking the term for frequency of use in a known context and adding the term in the known context to the training example with a new priority if the frequency has reached a predetermined threshold; and recompiling the language model based on the term in context.

In another aspect, the disclosure relates to a method of removing terms from a language model based on use. The method includes receiving text from a plurality of platforms; determining whether the text includes a term in a stored data model; if the term is in the data model, determining a frequency of use of the term in the text in a context in which the term appears in the data model; deleting the term in context from a training example for the data model if the frequency of use falls below a predetermined threshold; and recompiling the language model based after removing the term in the context from the training example.

Further embodiments, features, and advantages of the system and method for a system and method for automatically prioritize language mode and ontology expansion and pruning, as well as the structure and operation of the various embodiments of the system and method for a system and method for automatically prioritize language mode and ontology expansion and pruning, are described in detail below with reference to the accompanying drawings.

BRIEF DESCRIPTION OF THE DRAWINGS

The accompanying figures, which are incorporated herein and form part of the specification, illustrate the system and method for automatically prioritize language mode and ontology expansion and pruning. Together with the description, the figures further serve to explain the principles of the system and method for automatically prioritize language mode and ontology expansion and pruning described herein and thereby enable a person skilled in the pertinent art to perform and use the system and method for automatically prioritize language mode and ontology expansion and pruning.

DETAILED DESCRIPTION

Reference will now be made in detail to embodiments of the system and method for a system and method for automatically prioritize language mode and ontology expansion and pruning with reference to the accompanying figures. The same reference numbers in different drawings may identify the same or similar elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Figure 1:
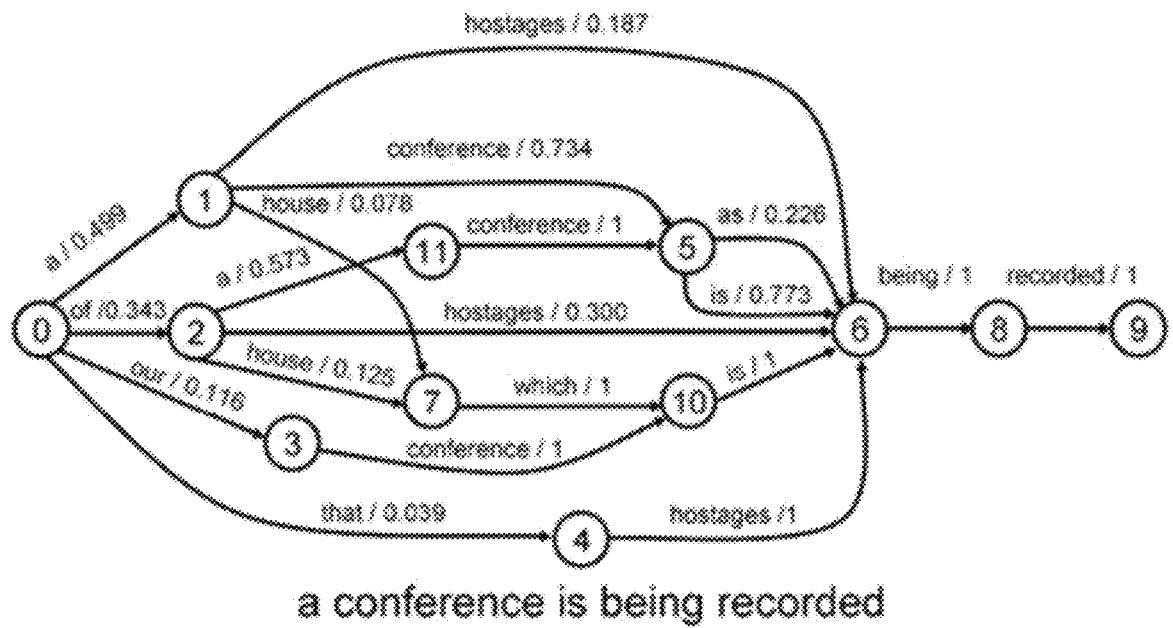
FIG. 1 is an example of a word lattice.

To create a language model (LM) for use in a specific domain, texts are gathered from various sources such as websites, chat logs, call logs, documentation, and other sources in that domain. Once the texts are aggregated, LM construction toolkits such as the CMU [1], SRI[2], or IRST [3] are applied to the data. They extract the vocabulary used within the texts and the statistics of their use with other vocabulary, such as unigrams, bigrams, and trigrams. These statistics can then be used to calculate a priori statistics of sentences that can be formed using the known vocabulary, which are organized in a lattice. A word lattice is an acyclic directed graph with a single starting node and edges labeled with a word and its corresponding probability of following the current word in the source texts. By following a path through the lattice from the starting point to any particular node, the a priori probability of that series of words (i.e. a sentence) appearing in the domain specific texts can be calculated. In the case of FIG. 1, the subject phrase is "a conference is being recorded." An example of algorithms as applied to traverse a word lattice can be found at https://www.slideserve.com/kipling/an-evaluation-of-lattice-scoring-using-a-smoothed-estimate-of-word-accuracy, which is incorporated herein in its entirety as background information.

A different approach to modeling word usage in context is to construct vectors to represent each word in a N-dimensional vector space. These vectors are manipulated during training based on observing where terms occur in the context of the surrounding terms. Terms that occur in the same context are moved closer to alignment. Terms that do not occur in the same context are moved further away. Once trained, the set of vectors can be used to reason about the similarity of words by performing vector arithmetic, such as measuring the distance between two points in the vector space. This approach is known as word embeddings [4], and is a way to group similar terms in a corpus together. Both the LM and word embedding approaches are unsupervised in that they require no human effort to construct. The training algorithms are simply given large training corpora and they use term positions and statistics within the corpora to build a model.

In contrast to models showing the statistical relationship between terms in a training corpora, data modeling approaches seek to define deeper relationships between terms such as hierarchies and negations. For such models there are two common structures used. The simpler form is a taxonomy, which is simply a tree of entities that form a hierarchy. For example, you could create a taxonomy of food where the entities are individual food items such as cheddar cheese, peas, corn, apples, pork, skim milk, etc. You would then create low level classes of foods like red meat, white meat, all cheese, all milk, families of fruits and vegetables, etc. Then you group all of the specific individuals into the classes they belong. Next you create higher level classes such as meat, fish, dairy, fruit, vegetables, etc. and group the classes of foods into the higher level classes. Finally, you can create the top layers of animal products, and non-animal products and put them under the root node of food. In this way you have constructed a taxonomy of food that you can go from specific examples to more and more general classes by following the tree backwards. You can also do simple reasoning like parent-of or sibling-of relationships, and find the least common ancestor between two individuals, like animal products for milk and pork.

For many cases this tree structure is enough to model data and process it. But more complicated relationships, like multiple inheritance and applying logical assertions, require storing data and meta data in a graph form. This is where ontologies come in. An ontology is a directed graph with four primary components: individuals, classes, attributes, and relations. There are many more components possible like events and restrictions as well. Ontologies allow for very rich data modeling with complex relationships and logical inferences about the data. There are many ways to construct ontologies and several different syntaxes for expressing and storing them. Taxonomies and ontologies typically require some human effort to construct. They may be seeded by some statistical observations from corpora, but the relationships between terms are usually defined or refined by humans. These models are concerned with the logical inference that can be drawn from terms within them and therefore require at least some logical relations to be encoded within them by humans.

Figure 2:
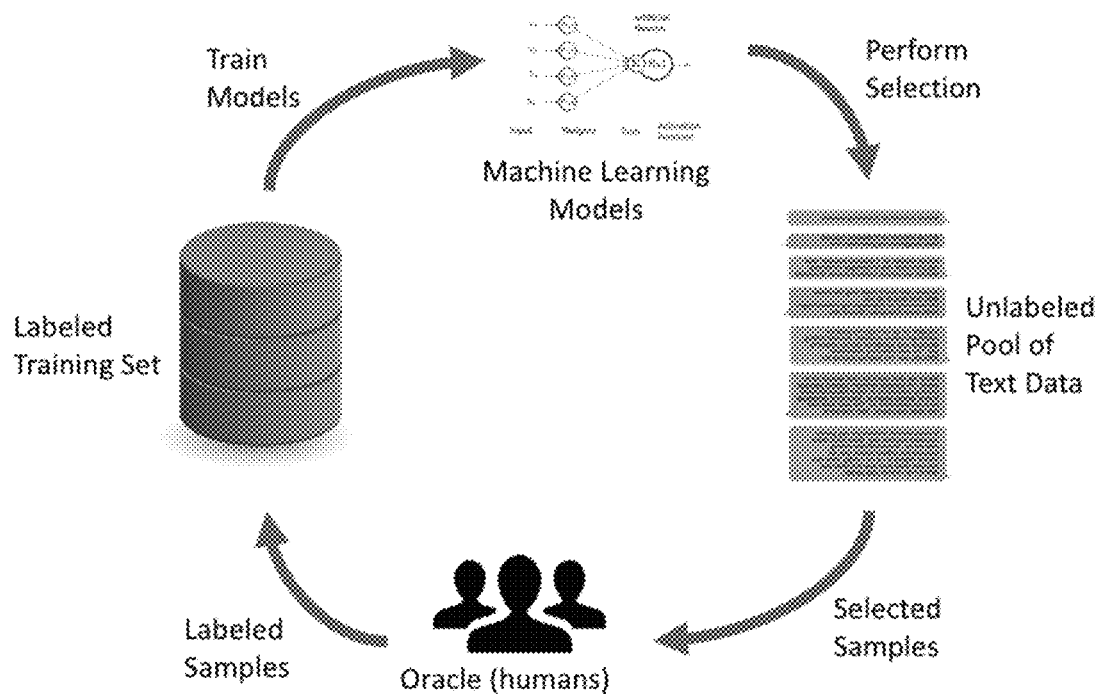
FIG. 2 illustrates an active learning process according to principles described herein.

Human-in-the-loop (HITL) is a subfield of Machine Learning where the model requires some form of human interaction. A common HITL approach is known as Active Learning. With active learning an existing model is supplied with a large pool or stream of unlabeled samples. The model then chooses which samples it thinks would be most informative to know the label for based on a selection strategies, of which there are several commonly used. Human oracles are then shown the selected samples and give them labels. These labeled samples are added to the training data to retrain the model from. In this way the model will learn more quickly from less training data then given a large sample of labeled results that contain many duplicated features. This active learning process is shown in FIG. 2.

Language model and ontology refinement for Intelligent Virtual Assistants (IVAs) is described herein. It is not necessary for the IVA to understand every possible word in order to understand a user's intention in a query. Computational overhead of unbounded LMs and data models will increase understanding latency. However, some words, such as those referring to products or services, are important to understand.

Therefore it is desirable to monitor user communication channels for new terminology that should be understood. Personal communication texts such as emails, instant messaging, and social media are particularly challenging due to their open vocabulary that continuously grows. There are constantly new products, applications, devices, terminology, slang and abbreviations being created and used within such communication channels. In order to deal with the evolving nature of internet language in a timely fashion, automated methods to detect high value words for insertion into LMs and data models are needed. Conversely, words that fall out of use, such as discontinued products or cultural references that are no longer popular, should be removed to maintain the size of models and speed traversals through them.

Herein a system and method to detect and prioritize insertions of new terminology into language and data models. Also provided herein are a system and method to prioritize removal of unused terms from such models to limit their growth and searching latency. In order to discover new terms to add to the IVA's knowledge, several content streams may be monitored. For example, one stream may be trending topics in social media platforms. These may originate from Twitter, Facebook, Pinterest or similar sites where users are actively communicating around topics. As topics gain popularity, they begin to "trend" by rising to the top of the subjects or topics that people are communicating about.

For example, during the holiday season there are new products such as toys and electronic devices that are released to take advantage of the seasonal increase in consumer spending. Suppose one such product is a new smart phone device such as the Google Pixel. When the device is announced or released, there is a sudden emergence in conversations around the topic of the Pixel, where before the term was not related to the electronics domain at all, or may not have even existed if it is an original name. By monitoring trending topics we will observe a sudden appearance of an unknown term, or a term that is not previously associated to the context it appears in.

In a second example, suppose a tropical storm has appeared and is making landfall. Tropical storms are commonly named and if the storm is expected to have a large impact on a populated area many news sites and, therefore, social media sites will experience a sudden spike in conversations around this new name. For IVAs in the travel domain, it will be helpful that these events are understood quickly as many travelers will begin to ask about disruptions caused by the storm.

Additional content streams can be customer e-mail and live chat transcripts, or any other form of customer to company communication channels. For weather occurrences, feeds such as the NOAA and Weather Channel can be monitored. News sites and aggregates of new feeds can also be ingested. From these sources without the construct of trends, terms can be counted over a sliding time window such as a day or week to create a set of trending terms.

Regardless of the source, when new terminology appears in trends we first consult the existing LM and data models used by the IVA. If the term is unknown to the LM it must be prioritized for addition. This prioritization can be based on any predetermined characteristic, e.g., frequency, topic, or source. For example, a frequency chart of mentions across multiple channels/source may be populated to determine the prevalence of the new term. For example, if a new term is only trending within a specific source such as Twitter, it may refer to some isolated phenomenon that may not be as important to be known by the IVA.

On the other hand, a new term may be important for the IVA to know to facilitate handling of incoming customer communication. An example of such phenomenon was the volcanic events that occurred in Iceland in 2010, which caused an ash cloud that grounded air transportation in Europe and caused a spike in the usage of terms such as "ash" and "volcano" that were previously very low ranked in IVAs for airlines. In the case of a tropical storm name or highly anticipated new product, the term might have been previously heard by the IVA (such as tropical storm name "Michael"), the term should be temporarily highly ranked across multiple sources, i.e., much higher and in a different way than the given name "Michael" might previously have been encountered in the existing ontology. That is, the context for an existing term has changed.

We can use this coverage of trending terms across multiple sources, e.g. external to the IVA or in conjunction with the IVA, to inform the usage of terms and to prioritize their addition to or usage in the data model/language model. For example, the frequency with which a term appears, context, and/or threshold counts can factor in the prioritization/ addition of a term. In one aspect, a human could provide input for retraining the model based on new terms, including recommending a new term's priority and how that term should be deployed to the IVA. In the inverse, a term could be removed or priority reduced based on these factors, for example, when the volcano eruption is no longer a factor in air travel or the hurricane has passed, as discussed further below.

Figure 3:
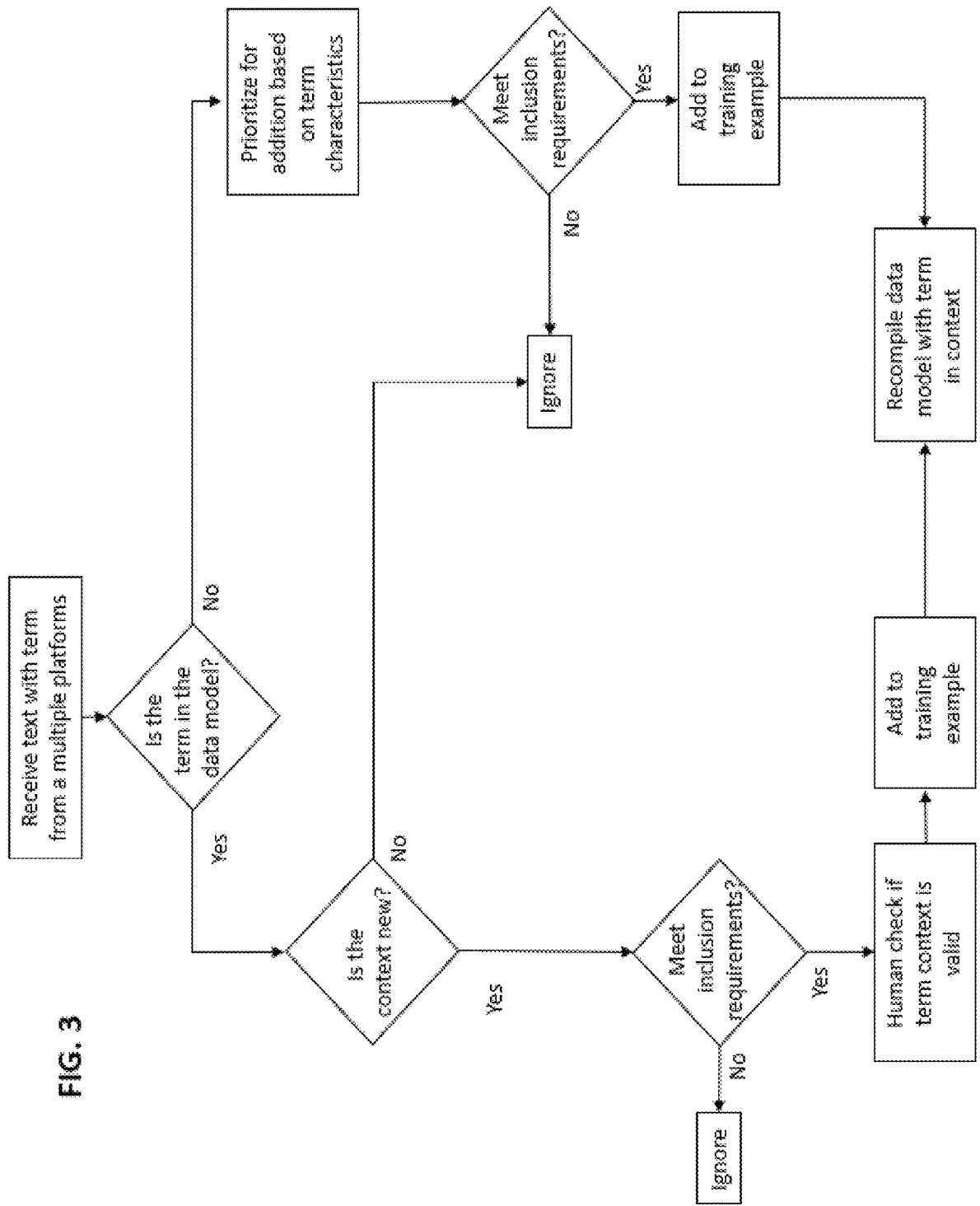
FIG. 3 is a flowchart showing an example set of steps for performing a method as described herein.

In some cases the term will be known, but the context it appears in is new. In the above Google Pixel example, the word "pixel" may already appear in the IVA's vocabulary, but in its ontology it is used for display or camera resolution. To detect usage, we can create embedding models from sliding windows of time using the text from the various input sources. If the existing term becomes embedded along with words that were not previously associated with the term, such as "iPhone", "Apple", or "Google" in the case of the Pixel, we can determine that the new usage of the existing term indicates a new object. In these cases the ontology or other data models will need to be updated to reflect the alternative usage and this update will be prioritized the same way as a new term. Once terms cross a predefined threshold, which is adjustable based on the availability of human annotators, they are given to a human along with example context to be added to the data models and/or LMs. This process of the model selecting its own training data is a special case of HITL known as Active Learning [5]. The human will then add the term to the ontology or update the ontology to reflect the new usage of the existing term. For new terms they will need to be added to the LMs as well so that speech recognition engines will be able to decode the word successfully. A flow chart for an exemplary implementation is provided in FIG. 3.

For an IVA, how a new term is being embedded can be studied. For example, if we look at previous versions of a word lattice or word embedding model, new text can be fed into the model to see how existing terms are being embedded with respect to new pairs or strings of terms. New usage of a term can therefore be identified and its new meaning/usage incorporated into the ontology/language model. This allows for the new usage to be disambiguated based on context. For example, the term can be updated in the ontology and its meaning updated. Its appearance in the language model/ word lattice or word embedding model can therefore be changed to reflect the updated usage.

While monitoring streams of trending topics and terminology from various sources, a list of known vocabulary is maintained. This list reflects all terms known to the IVA through the LMs and data models. Each term in the vocabulary is associated to a timestamp of last mention. When a term is encountered in the input streams and it exists in the vocabulary, the timestamp associated to the term is updated. If a product is discontinued or a tropical storm passes over, we would expect the usage of such terms will diminish over time. Once a term has not been mentioned longer than some tunable cutoff period, over one year for example, it will be deleted from the LMs and data models of the IVA causing the IVA to "forget" the unused term. In this way terms that have a lifespan are not maintained in the LMs and data models, which will prevent unbounded growth and steadily increasing time to search and traverse the models. As the pruning requires no human intervention it can be done automatically, however human review can be used if desired to approve the modifications.

According to principles described herein, the time from when a new term enters use and its adoption by an IVA (or other language based system) can be reduced, thus causing an improvement in the functioning such a device.

According to principle described herein, a human may be involved in determining thresholds by which the system may then run automatically for addition of trending terms and removal of decreasing terms. In the case of addition, a human in the loop may improve retraining based on new terms because a human can provide context for use in retraining the model and recommend priority. Such human activity in conjunction with the automated system of language model and word embeddings described above, can increase the speed with by which the automated models can be retrained to account for trending and declining terms.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A computer-implemented method of automatically removing terms from a language model based on use, the method comprising:
    ingesting language data from internet-based content streams, wherein the internet-based content streams are specific to a domain of an intelligent virtual assistant (IVA);
    processing the language data using a language model toolkit to extract vocabulary from the language data, the extracted vocabulary comprising terms;
    identifying select terms by counting the terms in the extracted vocabulary over a sliding window;
    comparing the select terms from the extracted vocabulary to terms stored in a language model specific to the IVA to determine if the select terms have a match to the terms in the language model;
    determining usage of the select terms in context with respect to the language data using an embedding model;
    for any of the select terms that have a match in the language model, determining a frequency of use of the select term in the ingested language data in its associated usage in context;
    automatically deleting one or more first terms of the select terms from a training example for the language model without further human intervention based on the frequency of use of the one or more first terms falls below a predetermined threshold;
    recompiling the language model based on the training example after deleting the one or more first terms; and
    adopting the recompiled language model into the IVA.

2. The method of claim 1, further comprising adding one or more second terms the select terms to the training example if the frequency of use of the one or more second terms meets a second predetermined threshold.

3. The method of claim 1, wherein the predetermined threshold is determined automatically based on predetermined values stored in a digital storage device.

4. A computer program product for automatically updating a language model for an intelligent virtual assistant (IVA), the computer program product comprising computer executable instructions embodied in a non-transitory computer readable medium that, when executed by one or more processors, cause the one or more processors to:
    ingest language data from internet-based content streams, wherein the internet-based content streams are specific to a domain of the IVA;
    process the language data using a language model to extract vocabulary from the language data, the extracted vocabulary comprising terms;
    identify select terms by counting the terms in the extracted vocabulary over a sliding window;
    compare the select terms from the extracted vocabulary to terms stored in a language model specific to the IVA to determine if the select terms have a match to the terms in the language model;
    determine usage of the select terms in context with respect to the language data using an embedding model;
    for any of the select terms that have a match in the language model, determine a frequency of use of the select term in the language data in its associated usage in context;
    automatically delete one or more first terms of the select terms from a training example for the language model without further human intervention based on the frequency of use of the one or more first terms falls below a predetermined threshold;
    recompile the language model based on the training example after deleting the one or more first terms; and
    adopting the recompiled language model into the IVA.

5. The computer program product of claim 4, further comprising additional instructions embodied in the non-transitory computer readable medium that, when executed by the one or more processors, cause the one or more processors to to add one or more second terms the select terms in the known context to the training example if the frequency of use of the one or more second terms meets a second predetermined threshold.

6. The computer program product of claim 4, wherein the predetermined threshold is determined automatically based on predetermined values stored in a digital storage device.

7. A system for selecting actions to perform for an entity based on content items, the system comprising:
    at least one processor; and
    a memory storing instructions that, when executed by the at least one processor, cause the at least one processor to:
        ingest language data from internet-based content streams, wherein the internet-based content streams are specific to a domain of an intelligent virtual assistant (IVA);
        process the language data using a language model to extract vocabulary from the language data, the extracted vocabulary comprising terms;
        identify select terms by counting the terms in the extracted vocabulary over a sliding window;
        compare the select terms from the extracted vocabulary to terms stored in a language model specific to the IVA to determine if the select terms have a match to the terms in the language model;
        determine usage of the select terms in context with respect to the language data using an embedding model;
        for any of the select terms that have a match in the language model, determine a frequency of use of the select term in the language data in its associated context;
        automatically delete first terms one or more of the select terms from a training example for the language model without further human intervention based on the frequency of use of the one or more first terms falls below a predetermined threshold recompile the language model based on the training example after deleting the one or more first terms; and adopt the recompiled language model into the IVA.

8. The system of claim 7, the memory storing additional instructions that, when executed by the at least one processor, cause the at least one processor to adding one or more second terms the select terms in the known context to the training example if the frequency of use of the one or more second terms meets a second predetermined threshold.

9. The system of claim 7, wherein the predetermined threshold is determined automatically based on predetermined values stored in a digital storage device.

\* \* \* \* \*